US 6,623,497 B1

(12) United States Patent
Feingold

(10) Patent No.: US 6,623,497 B1
(45) Date of Patent: Sep. 23, 2003

(54) KERATOME WITHOUT APPLANATOR

(76) Inventor: Vladimir Feingold, 31732 Isle Vista, Laguna Niguel, CA (US) 92677

( * ) Notice: Subject to any disclaimer, the term of this patent is extended or adjusted under 35 U.S.C. 154(b) by 0 days.

(21) Appl. No.: 09/521,010

(22) Filed: Mar. 7, 2000

Related U.S. Application Data

(63) Continuation-in-part of application No. 09/132,987, filed on Aug. 12, 1998, now Pat. No. 6,083,236.

(51) Int. Cl.[7] .................................................. A61F 9/00
(52) U.S. Cl. ...................................................... 606/166
(58) Field of Search ................................. 606/166, 169, 606/107, 172

(56) References Cited

U.S. PATENT DOCUMENTS

| | | | |
|---|---|---|---|
| 4,662,370 A | | 5/1987 | Hoffmann et al. |
| 4,807,623 A | * | 2/1989 | Lieberman .................. 606/166 |
| 4,903,695 A | | 2/1990 | Warner et al. |
| 5,063,942 A | | 11/1991 | Kilmer et al. |
| 5,133,726 A | | 7/1992 | Ruiz et al. |
| 5,288,292 A | | 2/1994 | Giraud et al. |
| 5,318,044 A | | 6/1994 | Kilmer et al. |
| 5,318,046 A | | 6/1994 | Rozakis |
| 5,342,378 A | | 8/1994 | Giraud et al. |
| 5,368,604 A | | 11/1994 | Kilmer et al. |
| 5,395,385 A | | 3/1995 | Kilmer et al. |
| 5,496,339 A | | 3/1996 | Koepnick |
| 5,527,328 A | | 6/1996 | Pintucci |
| 5,556,406 A | | 9/1996 | Gordon et al. |
| 5,586,980 A | | 12/1996 | Kremer et al. |
| RE35,421 E | | 1/1997 | Ruiz et al. |
| 5,595,570 A | | 1/1997 | Smith |
| 5,624,456 A | | 4/1997 | Hellenkamp |
| 5,658,303 A | | 8/1997 | Koepnick |
| 5,690,657 A | | 11/1997 | Koepnick |
| 6,051,009 A | | 4/2000 | Hellenkamp et al. |
| 6,165,189 A | * | 12/2000 | Ziemer ........................ 606/166 |

FOREIGN PATENT DOCUMENTS

| | | |
|---|---|---|
| DE | 197 46 038 A1 | 4/1998 |
| FR | 2 595 243 | 9/1987 |
| WO | WO 90/01905 | 3/1990 |

* cited by examiner

Primary Examiner—Kevin T. Truong
(74) Attorney, Agent, or Firm—Lawrence S. Cohen

(57) ABSTRACT

A keratome for performing corneal resectioning which functions without a need for a surface against which to press the subject cornea during surgery, facilitating access for the surgeon and reducing or eliminating mechanical part rubbing near the surgical site. The keratome has a positioning ring to position an eye with the cornea protruding through and restrained by the ring. A blade is preferably suspended from its ends by a blade support which is driven by a drive mechanism, and a guide is disposed substantially parallel to the blade. The blade describes a forward path above and at a controlled distance from the positioning ring while also oscillating laterally. A guide may be disposed parallel to the blade edge to control resectioning thickness. Drive control and vacuum for the positioning ring are provided under user command by a control unit having user inputs.

22 Claims, 9 Drawing Sheets

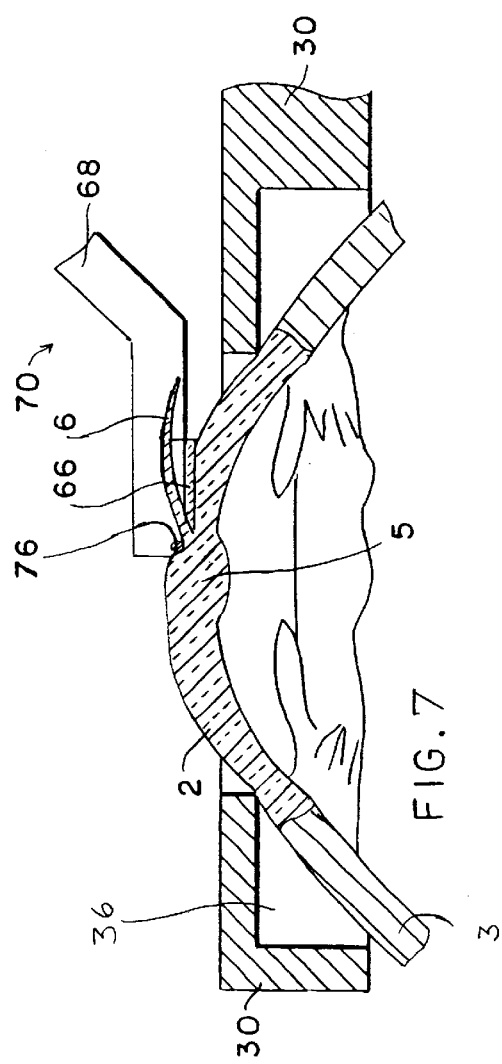
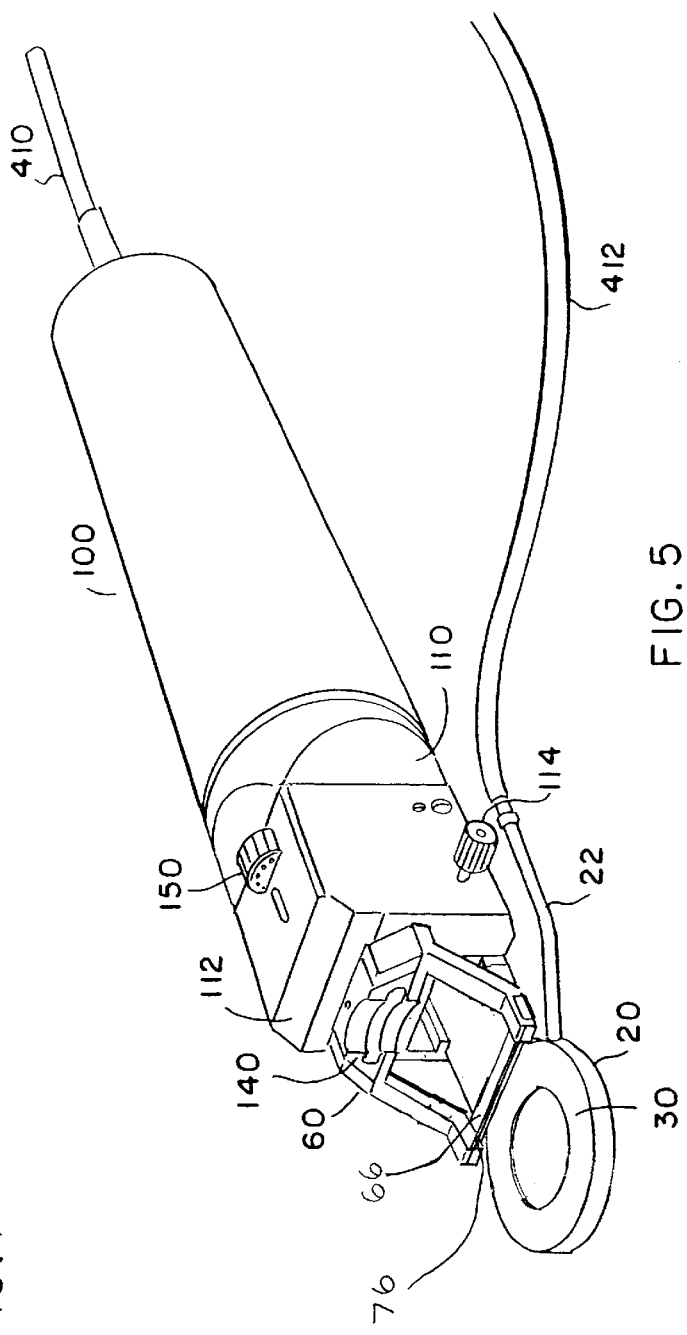

KERATOME WITHOUT APPLANATOR

The present application is a continuation-in-part of U.S. patent application Ser. No. 09/132,987 filed on Aug. 12, 1998, now U.S. Pat. No. 6,083,236 which is incorporated herein by reference.

FIELD OF THE INVENTION

The present invention pertains to the general field of ophthalmologic surgical devices, and more specifically to the field of devices for performing corneal resectioning and methods therefor.

BACKGROUND

Numerous ophthalmic surgical procedures, such as for correcting myopia or hyperopia, require one or more steps of resectioning the cornea of the eye. A variety of devices called keratomes have been developed over recent decades to perform such corneal resectioning. Referring to FIGS. 1, 2a and 2b, a typical resectioning operation will separate flap 6 of corneal tissue 2 from eyeball 4. The tougher outer layers of epithelial cells 8 are separated and lifted away to expose the more compliant inner layers 12 of cornea 2, but the separated outer layers are left attached as flap 6. Once exposed, interior layers 12 of cornea 2 will to some extent adjust themselves, or their shape may be altered through further surgical steps. Such further steps may include, for example, making radial keratotomy cuts or performing a subsequent resectioning which may include removing a contoured layer of corneal tissue. At the conclusion of the various steps of the surgical procedure, flap 6 is typically replaced over inner corneal tissues 12 to protect the healing tissues.

The representative keratomes described in U.S. Pat. No. 5,496,339 issued to Koepnick, and U.S. Re. Pat. No. 35,421 issued to Ruiz et al., which are depicted in FIGS. 3a and 3b, demonstrate many standard features of prior art keratomes. A retaining ring for positioning and retaining the subject eyeball is typically supplied with a source of vacuum. The vacuum pressure draws the eyeball into the retaining ring so that the cornea protrudes through the retaining ring and presses against the surface of a feature, herein referred to as an applanation shoe, which is provided to restrain the protruding cornea. An applanation shoe has been found important in all known prior art.

However, an applanator impedes access to the eye under surgery. One approach to this problem is to make the applanator pivotable, or otherwise disengageable from contact with the eye, without a need to disengage the entire surgical apparatus from its positioning on the eye.

In order to resection the cornea, a cutting blade must be drawn through the corneal tissue, and both the thickness and the expanse of the corneal tissue which is cut must be carefully controlled. The separated portion of the cornea is typically left attached along one edge to form flap 6 which can easily be replaced over the cornea after the surgery.

Keratomes must have a mechanism by which the knife blade is guided. Proximate to the cutting location, the prior art keratomes all have blades rubbing on guides, or metal rubbing on metal, such as drive gears. Unfortunately, such rubbing can result in shavings being created and entering the surgical site. Referring to FIG. 3a, the keratome of Ruiz et al. has an intricate mechanism with metal-on-metal gears rubbing in the surgical vicinity. For example, pinion 834 rides on track 891 which is part of positioning ring 890; and endless pinion 822, along with its eccentric shaft and associated pinions, operates directly above the blade cutting site (not shown). In FIG. 3b, the keratome of Koepnick is seen to have blade 954 which rubs directly on the insert 948 and slides in surfaces defined along line 991. The sliding surfaces at 991 are located directly above positioning suction ring 990, and the rubbing surface between blade 954 and insert 948 is directly adjacent regions of intimate contact between the corneal tissue and insert 948. Thus, these two prior art keratome examples have rubbing between the cutting blade and other surfaces, and rubbing of gears, very close to the surgical site.

Another drawback of existing keratomes is the inconvenience of maintaining surgical cleanliness. Since parts of the keratome must be in intimate contact with tissues around and including the surgical site, it is necessary to ensure a high degree of cleanliness and sterility. The relatively intricate mechanisms which prior art keratomes position near the surgical site, as described above, have not been well-adapted for ease of cleaning and autoclaving.

Thus, a need exists for an easily used keratome able to perform precise resectioning operations, while facilitating surgical cleanliness by avoiding creation of shavings which might contaminate the surgical site, and by being easily cleaned, sterilized, and replaced.

SUMMARY OF THE INVENTION

A keratome in accordance with the present invention enables an ophthalmologic surgeon to perform corneal resectioning, separating a flap of corneal tissue for later replacement, without a need for an applanator, and without any rubbing of parts of the surgical device near the surgical site.

In accordance with the present invention, the surgical device preferably includes a surgical unit having cutting head elements mounted on a drive assembly, and also includes a control unit and a foot pedal. During surgery, the cutting head elements are in intimate contact with the subject eye, for positioning and cutting. The drive assembly element supports and drives the cutting head elements. The control unit is the preferred source of power and vacuum for the surgical unit, and it supplies power and vacuum according to settings entered by the user. The foot pedal allows the user to give commands to the surgical device without requiring use of hands. The surgical unit is preferably hand-held and easily positioned over the subject eye.

The preferred surgical unit includes three distinct elements. Two of these are "cutting head" elements which must contact the eye during corneal surgery—a positioning ring assembly and a blade fork assembly. These two cutting head elements extend from the third element, a drive assembly, in such a way that interference and rubbing between the cutting head elements proximal to the surgical site is minimal or entirely absent. Preferably, the two cutting head elements are easily removed and as easily replaced onto the third element, the drive assembly, without a need for tools, so the surgeon can ensure sterility by simply attaching fresh and sterile replacements for the cutting head elements.

In a preferred embodiment of the present invention, a blade fork assembly suspends a cutting blade between the positioning ring and the applanation shoe and guides the cutting blade near to the applanation shoe. The thickness of the cut is preferably controlled by a guide, which is disposed a controlled distance away from the cutting blade. The outer layer of corneal tissue is separated by the blade as it passes between the blade and the guide, so that the thickness of the separated layer is controlled by the spacing between the blade and the guide.

The blade fork assembly is caused to move by the drive assembly, which imparts two distinct movements to the blade fork assembly during cutting action. One movement is a high-speed lateral oscillation, and the other, imparted at the same time, is a slow smooth forward movement. The drive arm impel the blade fork forward as long as it is commanded to do so through the control unit, until the drive arm impinges on an adjustable stop mechanism, thereby causing a clutch to slip and preventing further forward displacement of the drive arm.

The blade assembly is preferably entirely suspended and does not touch any part of the mechanism which is near to the surgical site except indirectly by way of the blade fork drive arm which supports the blade assembly.

BRIEF DESCRIPTION OF THE DRAWINGS

FIG. 5 shows the surgical unit, with the cutting head elements attached to the drive assembly.

FIG. 7 shows an eye in a positioning ring and a blade cutting a corneal flap with thickness controlled by a guide.

DETAILED DESCRIPTION

The present invention.is described below by examples which include the best mode known, but such description is not to be taken as limiting the invention, which is defined separately in the claims.

Figure 1:
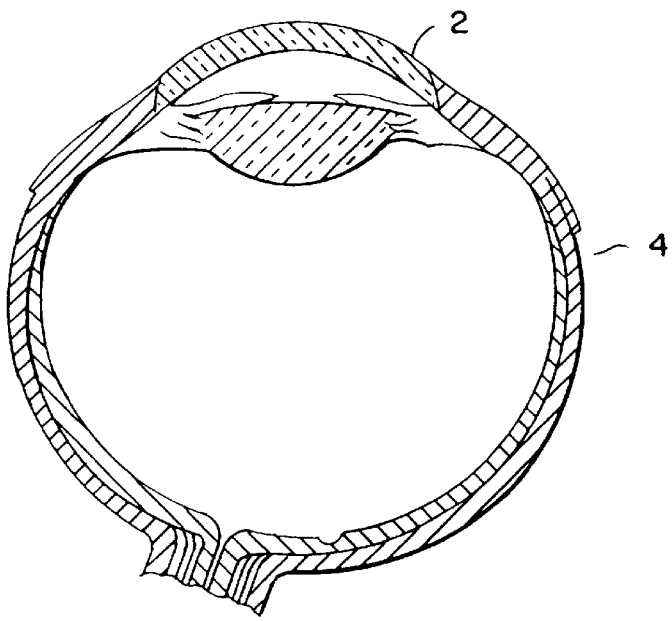
FIG. 1 is a cross-section of an eye.
Figure 2A:
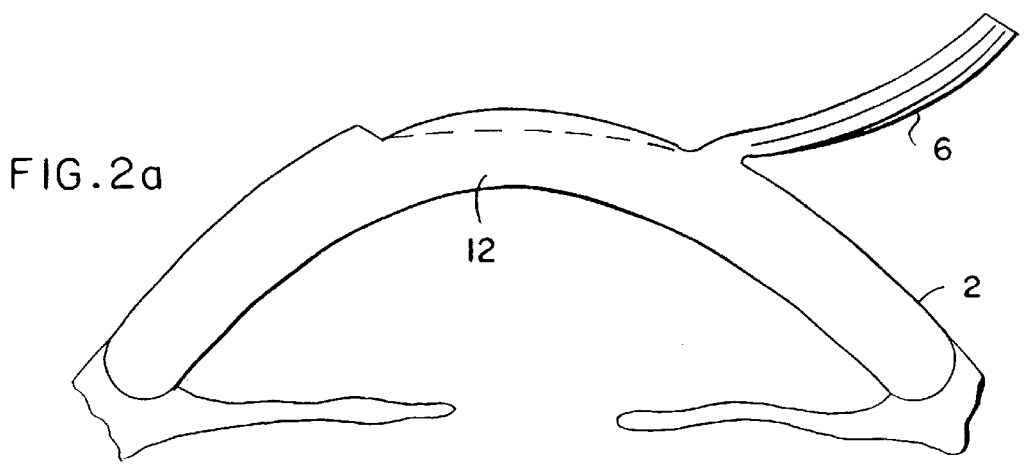
FIG. 2a shows a cornea with a flap of epithelial tissue lifted.
Figure 2B:
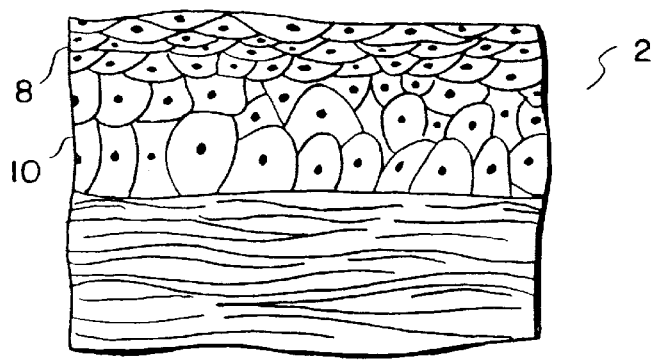
FIG. 2b is a representation of the variation of corneal tissue beginning at the outermost layers.
Figure 3A:
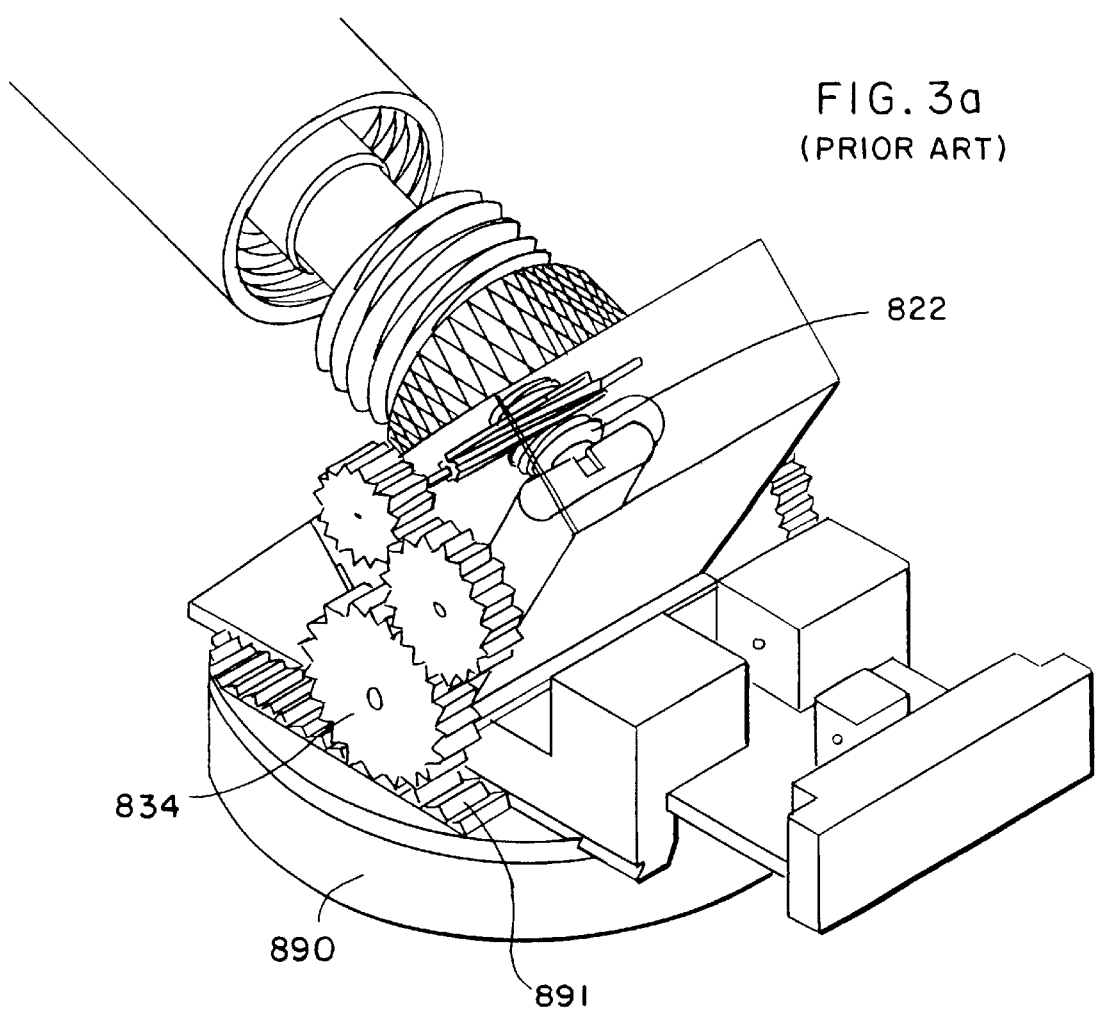
FIG. 3a shows the prior art keratome of Ruiz et al.
Figure 3B:
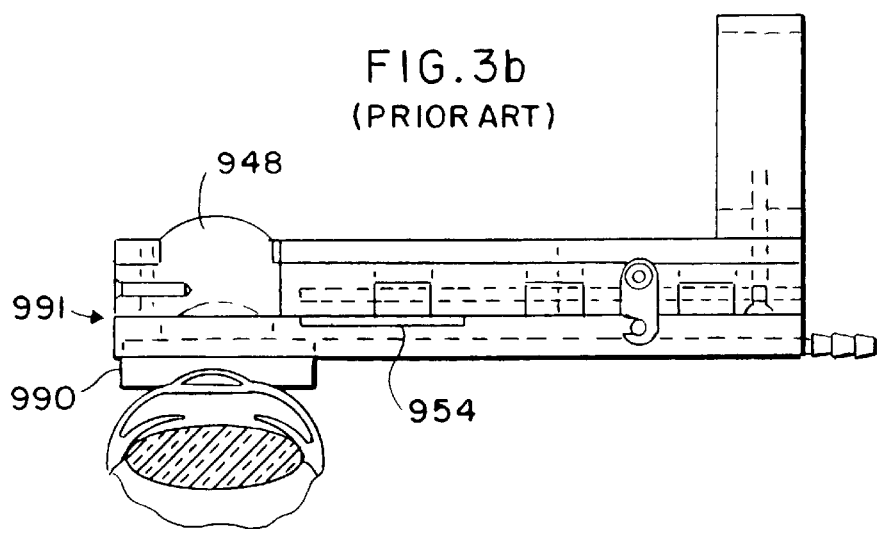
FIG. 3b shows the prior art keratome of Koepnick.
Figure 4:
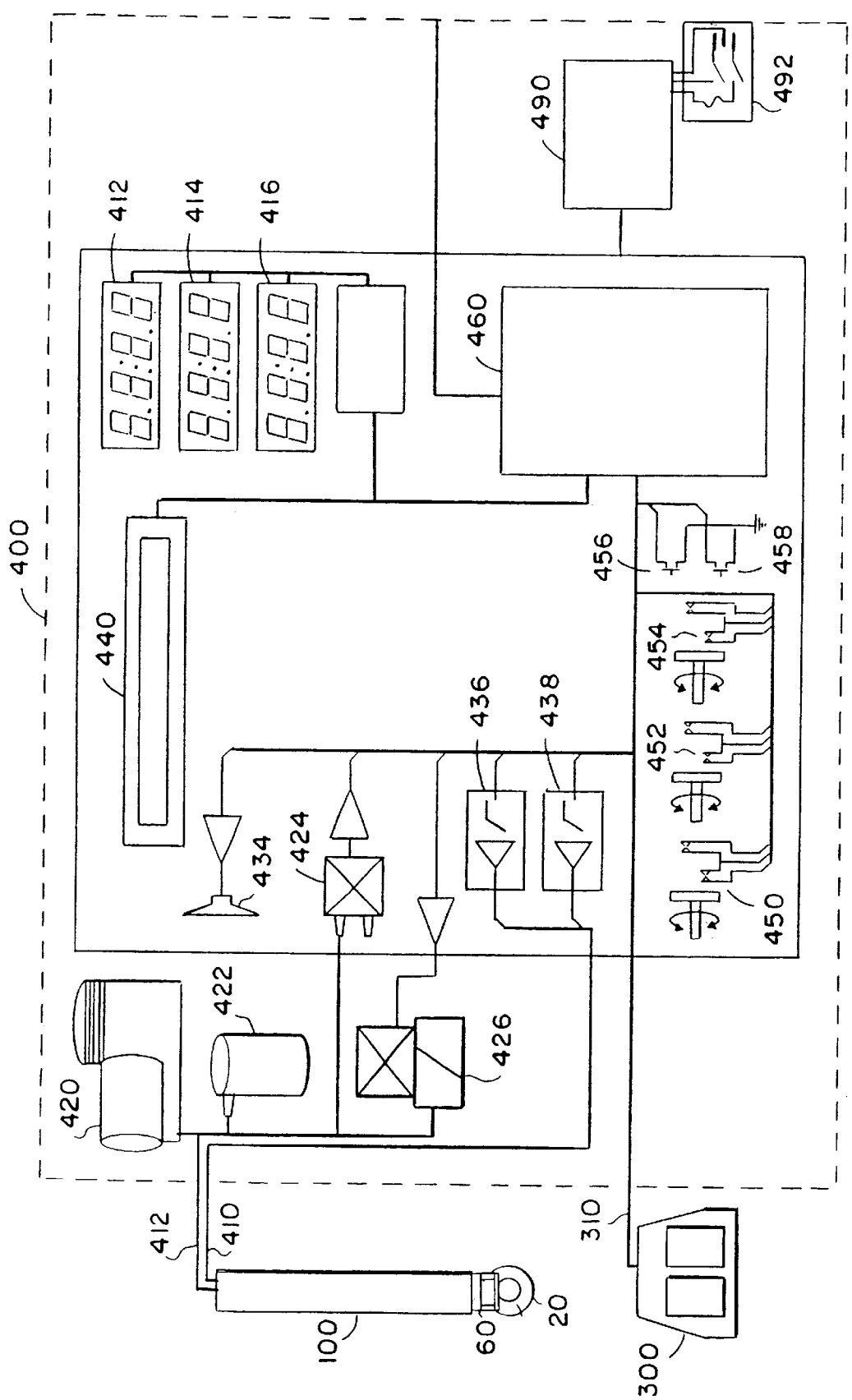
FIG. 4 shows the control unit with connections to the surgical unit and to a foot pedal.

Referring to FIGS. 4 & 5, the present invention is preferably embodied in three separate components: surgical unit 100, foot pedal 300, and control unit 400. Surgical unit 100 has three subsections including drive assembly 110 and two cutting head elements: positioning ring assembly 20 and blade fork assembly 60. Foot pedal 300 communicates user commands to control unit 400 via cable 310, and surgical unit 100 is connected to control unit 400 by electrical cable 410 and vacuum hose 412. Each of these items are discussed in more detail below.

Control Unit

The following describes a preferred embodiment of the invention with reference to FIG. 4. Control unit 400 is a microprocessor-controlled unit enabling the user to direct operation of the actuators within drive assembly 110 and the level of vacuum supplied to positioning ring assembly 20 of surgical unit 100. The user controls operation by means of two pedal switches of foot pedal 300, in conjunction with three rotary input devices 450, 452 and 454 and two pushbuttons 456 and 458 on the front panel of control unit 400. Operating parameters are displayed on the front panel for the user by means of numeric readouts 412, 414 and 416 and by multiple character alpha-numeric display 440, while speaker 434 gives audible information.

A microprocessor on printed circuit board 460 executes operating firmware which is held in reprogrammable non-volatile memory and can be reprogrammed in the field. The firmware allows the microprocessor system to read switch closures and the rotation of the rotary controls. These electronics translate operator actions into tool control voltages which are applied to the drive unit actuators and can be stored as presets to be recalled as required by the operator. The microprocessor system also interprets the sensors and controls the actuators to maintain vacuum at a level set by the user.

Control unit 400 provides electric control signals to surgical unit 100 via cable 410. Vacuum pressure for positioning ring assembly 20 is supplied from control unit 400 via vacuum hose 412. Control unit 400 contains vacuum reservoir 422 in which vacuum pressure is established by vacuum pump 420 and released by vacuum release solenoid 426, and the vacuum pressure is sensed by vacuum transducer 424 to give feedback to the control electronics. Electric control for the actuators (not shown) within drive assembly 110 is provided by electronic switches 436–438. Persons skilled in the art will appreciate that there is no limit to the variations by which control unit components may control the surgical unit actuators and vacuum.

Surgical Unit

Referring to FIG. 5, surgical unit 100 includes drive assembly 110 for supporting and driving the cutting head elements which contact the eye during surgery, including positioning ring assembly 20 and blade fork assembly 60. Surgical unit 100 is supplied electrically via cable 410, and vacuum is supplied to positioning ring 30 via vacuum hose 412 which attaches to vacuum connection tube 22. Blade 66 will cut the corneal tissue in a flap of a thickness controlled by the spacing from blade 66 to guide 76.

Figure 6:
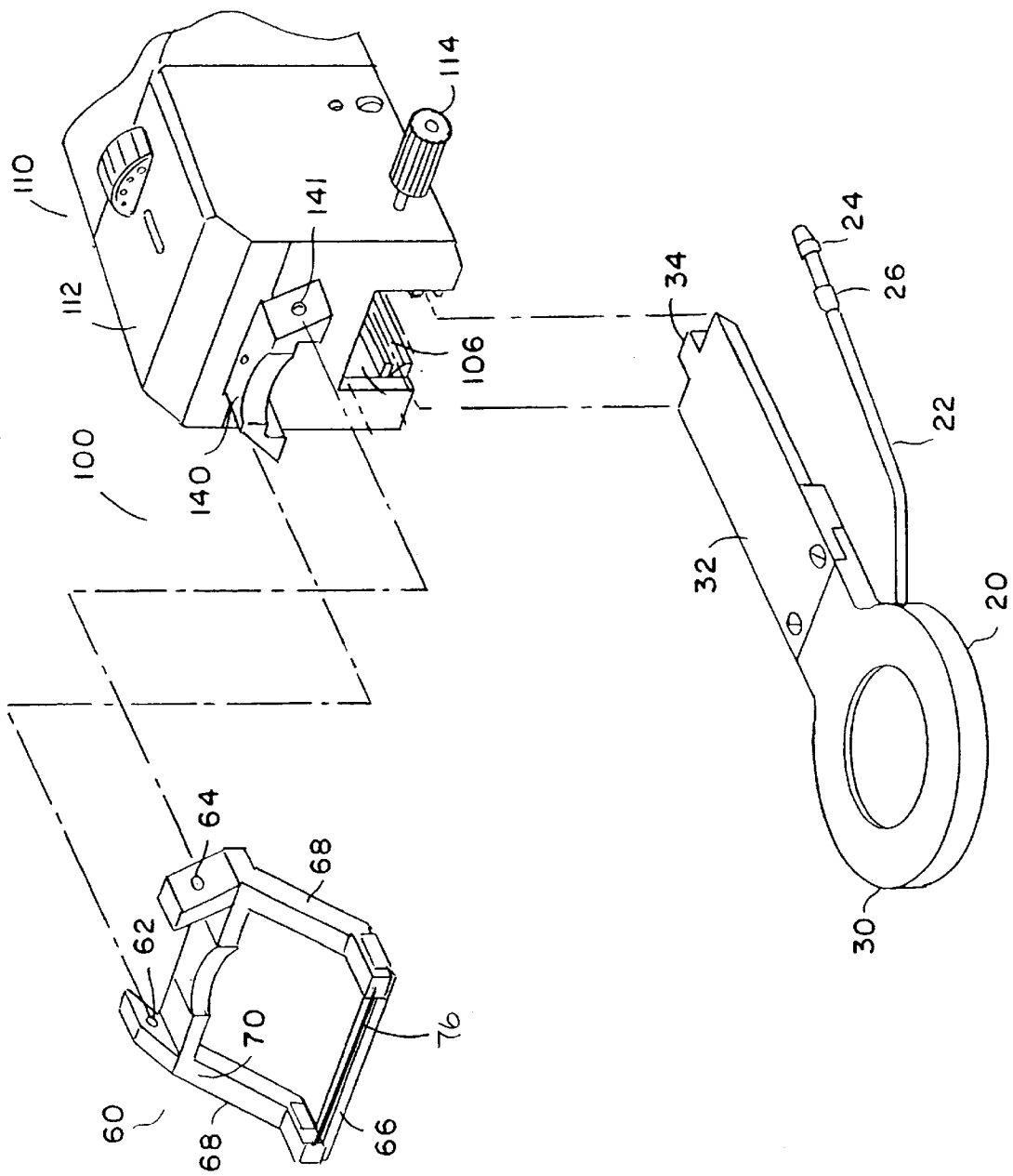
FIG. 6 shows the drive assembly front end with the cutting head elements detached therefrom.

FIG. 6 more clearly delineates the cutting head elements, positioning ring assembly 20 and blade fork assembly 60, as they are separated from front end 112 of drive assembly 110 without a need for tools. Since the cutting head elements ordinarily come into direct contact with a subject eye, it is preferable that they be removable and replaceable on drive assembly 110 without a need for tools, in order to facilitate the use of clean and sterile elements. For the same reason, it is also preferable that these cutting head elements be either sterilizable or sterile disposable.

Positioning ring support 32 preferably has tapered edges to mate with receiving feature 106 in drive assembly 110, with retention feature 34 also mating to a feature (not shown) of drive assembly 110. Positioning ring 30 may be restrained by thumbscrew 114. Blade fork 70 mates to drive arm 140, preferably using spring loaded ball detent assemblies 64 having a spring-loaded ball 62 to mate to drive arm notch 141. The three elements 20, 60 and 110 of surgical unit 100 are each described in more detail below.

Surgical Cutting Action

FIG. 7 shows the cutting head elements resectioning cornea 2. Vacuum pressure delivered to vacuum chamber 36 of positioning ring 30 will draw sclera 3 and cornea 2 of eye 4 upward to a stable position. Blade fork drive arm 140 (FIG. 5) supports blade fork 70 and imparts a compound movement to it. Blade fork 70 is oscillated rapidly in a direction parallel to the cutting edge of blade 66 (in and out of the page of FIG. 7), and simultaneously moved slowly forward (from right to left in FIG. 7), while maintaining blade 66 at a controlled distance from positioning ring 30. Blade 66, suspended from blade fork tines 68 along with guide 76, thereby separates a layer of corneal tissue 2 to form flap 6. The thickness of flap 6 is determined primarily by the spacing between blade 66 and guide 76, and to some extent by the guide and blade orientation and position. The forward travel of blade fork 70 continues until the formation of flap 6 is completed.

Blade Fork Assembly

FIG. 6 shows some details of blade fork assembly 60. A typical blade 66 and a representative guide 76 are shown suspended from blade fork tines 68. Optional spring detent insert 64 and the detent ball 62 of another spring detent insert are also shown. The detent ball of insert 64 will nest in notch 141 to releasably position blade fork 70 with respect to fork drive arm 140.

Figure 9A:
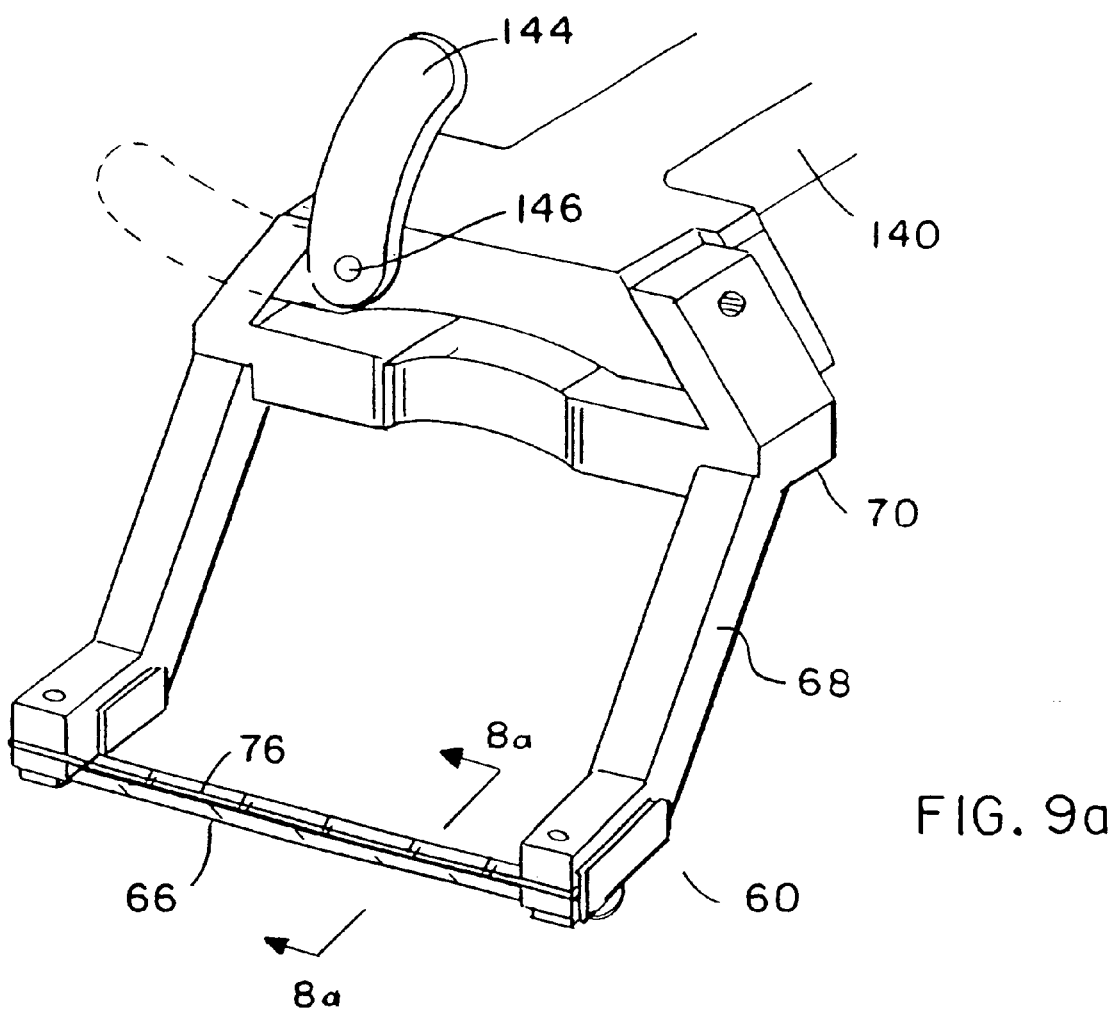
FIG. 9a shows a blade fork assembly with a cam lever securing it to the blade fork drive arm.

FIG. 9a shows blade fork assembly 60 suspending blade 66 and guide 76 from blade fork tines 68. Blade 66 and guide 76 are shown in cross section 8a—8a in FIG. 8a, and variations of the blade and guide arrangement are shown in FIGS. 8b, 8c, 8d, and 8e. In FIG. 9a, blade fork 70 is attached to drive arm 140 using a trapezoidal mating construction, and the trapezoidal attachment between blade fork 70 and drive arm 140 is secured using a locking lever 144 which actuates a locking cam (not shown) by rotating about pivot 146.

Figure 8A:
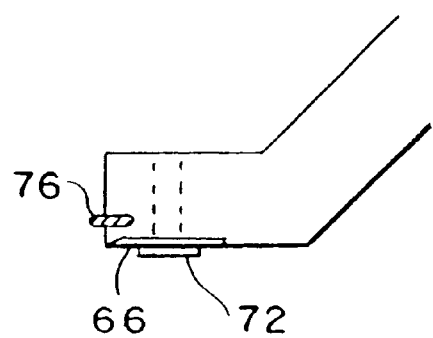
FIG. 8a shows details of section 8a—8a of FIG. 9a, including the blade.
Figure 9B:
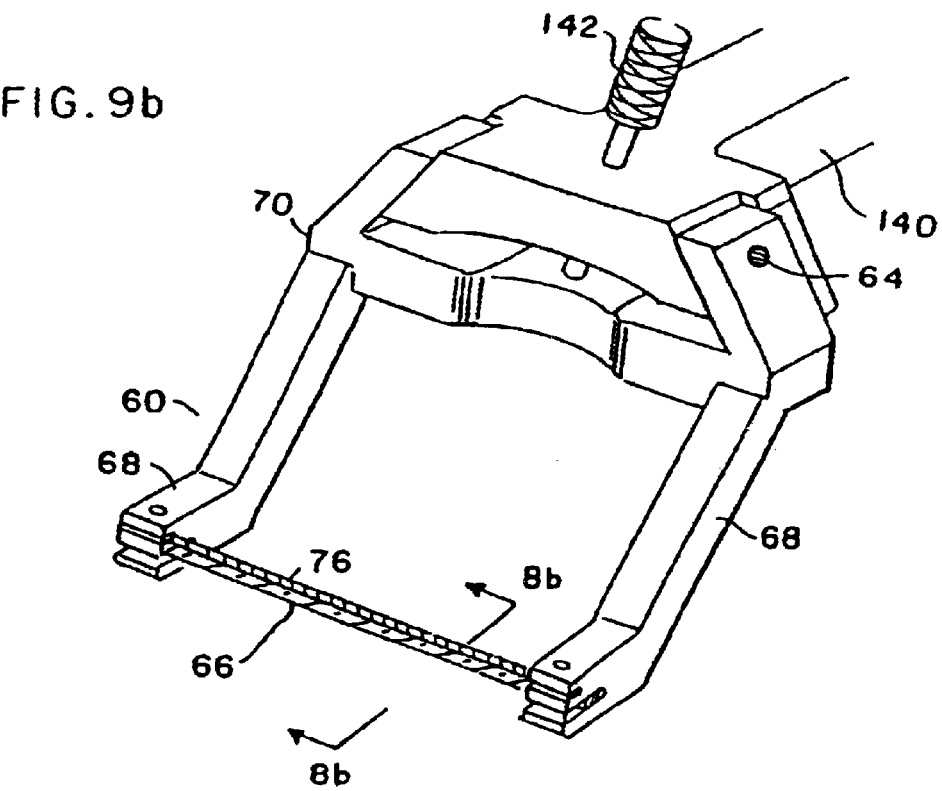
FIG. 9b shows a blade fork assembly secured to the blade fork drive arm with a thumb screw.

FIG. 9b shows blade fork assembly 60 alternatively secured to blade fork drive arm 140 by thumbscrew 142. Spring loaded ball detent assembly 64 helps establish and hold the positioning of blade fork 70 with respect to drive arm 140. As above, fork tines 68 suspend blade 66 and guide 76, which can be seen in cross section 8b—8b in FIG. 8b. FIGS. 8a, 8c, 8d and 8e show alternative examples of blade and guide arrangements which may be used.

Blade fork 70 is preferably composed of titanium but many other materials are suitable, including stainless steel. For a steam sterilizable blade fork, dimensionally stable plastics such as polycarbonate or polysulfone are suitable, and gas or gamma ray sterilization is compatible with additional plastics, such as polypropylene.

Blade 66 is preferably sapphire or similar crystalline materials, which is hard and strong and desirably transparent for the best visibility as the cutting operation progresses. Alternatively, and particularly for disposable versions, the blade may be surgical stainless steel or other suitable material.

The overall position of blade 66 and guide 76 with respect to positioning ring 30 is established by the combined positioning of blade 66 and guide 76 in blade fork assembly 60, by the relative positioning of drive arm 140 to positioning ring mounting features 106 (FIG. 6), and by the positioning ring 30 dimensions. However, this is a less critical relationship than in many keratomes, because the relationship between blade 66 and guide 76 primarily determines the corneal flap thickness.

FIG. 8a shows details of section 8a—8a of FIG. 9a, including guide 76 disposed parallel to blade 66. The spacing between guide 76 and blade 66 controls the thickness of corneal tissue cut, enabling the cut thickness to be controlled very precisely and also to be set under controlled conditions at the factory. Guide 76 has a cross-section defined in a plane perpendicular to the longitudinal axis of blade 66.

The perimeter of the cross-section of guide 76 is advantageously small, preferably less than 2 mm or less than 6 mm. A small cross-sectional perimeter conveys several advantages: it reduces the frictional interaction between the guide and the cornea, it localizes a deformation 5 (FIG. 7) of the cornea to avoid pressure on the eye generally, and it reduces the likelihood of trapped bubbles distorting the cornea to cause inaccurate cuts.

Figure 8C:
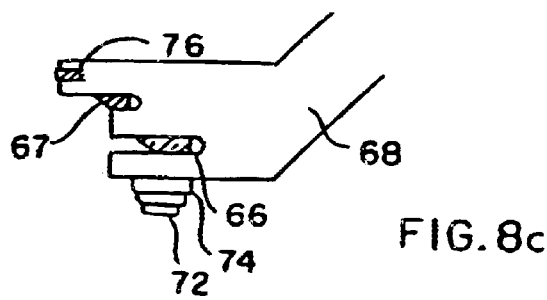
FIG. 8c shows an alternative dual blade and guide in a section similar to 8b—8b.
Figure 8B:
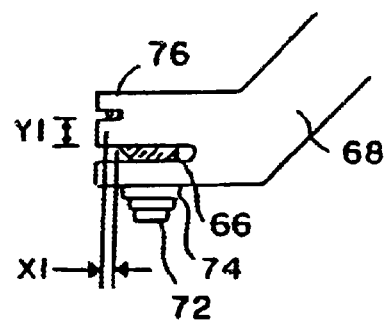
FIG. 8b shows details of section 8b—8b of FIG. 9b, including a stainless steel blade with guide.

FIG. 8b shows section 8b—8b, an arrangement of blade and guide for the blade fork assembly 60 shown in FIG. 9a. The leading edge of guide 76 is positioned very slightly forward (in the direction that the cutting head elements extend from the drive assembly) of the cutting edge of blade 66. Dimension x1 is the distance in the direction of blade travel between the leading edge of blade 66 and the leading edge of guide 76. The optimum length of dimension x1 depends on the orientations of the plane of blade 66 and, if applicable, of guide 76. Dimension x1 is preferably greater than zero, for example 0.20+/−0.05 mm or 0.30 +/−0.05 mm. Dimension y1, the distance between guide 76 and blade 66 in a direction perpendicular to the travel plane of blade 66, will vary depending upon the surgeon's needs, but will typically be made nominally 0.150 mm, 0.160 mm, 0.170 mm, or 0.180 mm, each nominal dimension being controlled to within a tolerance of preferably 0.030 mm or even more preferably 0.015 mm.

FIG. 8c shows, in a cross section similar to that of 8a—8a (FIG. 9a), an arrangement of blades 66 and 67 which may be suspended from blade fork tines 68. Here, lower blade 66 utilizes upper blade 67 as a guide for one flap of corneal tissue, while upper blade 67 utilizes guide 76 to control the thickness of a second flap of corneal tissue. Using this arrangement, a slice of corneal tissue of precise dimensions may be separated and then removed to accommodate an implant, leaving another flap 6 of the harder outer corneal tissue to cover the surgical site.

Figure 8D:
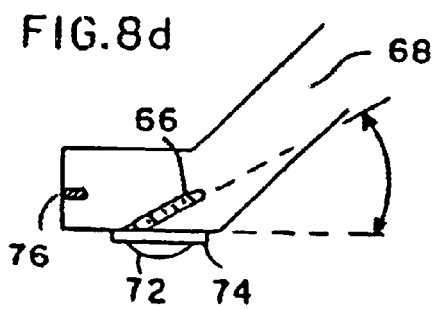
FIG. 8d shows an alternative angled blade and guide in a section similar to 8b—8b.

In FIG. 8d, blade 66 is shown having a small angle to the direction of travel, the angle preferably being about 25 degrees. Blade 66 is captured by screw 72 and washer 74, or suitable fastener. Flap thickness is controlled by the spacing from blade 66 to guide 76.

Figure 8E:
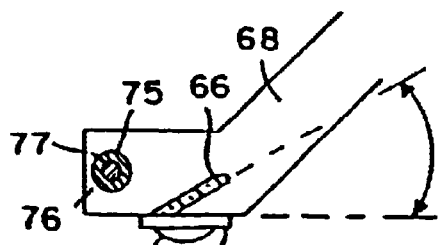
FIG. 8e shows an alternative blade and bearing guide in a section similar to 8b—8b.

FIG. 8e differs from FIG. 8d in that guide 76 comprises central core 75 and outer cylindrical bearing 77, which is preferably made of a tough, low friction material such as a plastic containing TEFLON™ material. If bearing 77 is shorter than guide core 76 by an amount equal to the maximum lateral oscillation amplitude of the blade assembly, then with this arrangement bearing 77 may slide very little, or not at all, on the corneal tissue. Rather, sliding may occur at the interface between core 76 and bearing 77, and bearing 77 may only roll on the corneal tissue.

Positioning Ring Assembly

FIG. 6 shows positioning ring assembly 20, including positioning ring 30, vacuum connection nipple 24, vacuum tube stop 26, and vacuum connection tube 22. These items supply vacuum to assembly 20 to draw a subject eye into position and restrain it.

Figure 10:
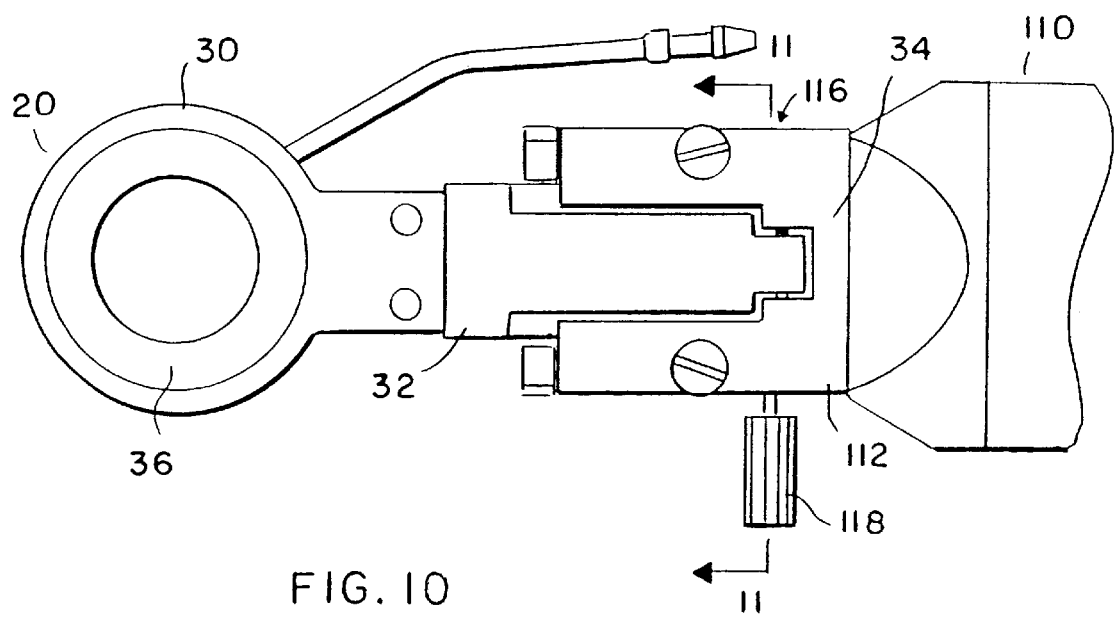
FIG. 10 shows the positioning ring releasably attached to the drive assembly.
Figure 11:
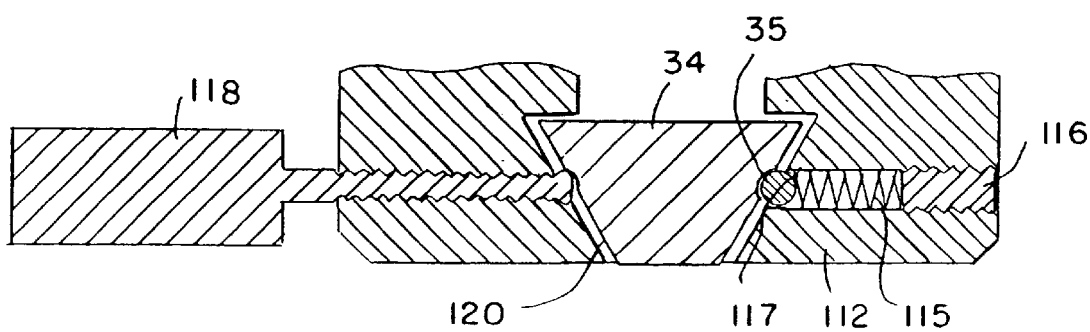
FIG. 11 shows details of positioning ring restraint at section 11—11 of FIG. 10.

FIGS. 10 and 11 depicts details of positioning ring assembly 20. Positioning ring 30 is provided with vacuum to vacuum chamber 36 so that an eyeball placed against it may be drawn in and restrained. The vacuum is furnished through vacuum connection tube 22, with the vacuum hose (not shown) placed over vacuum connection nipple 24 and stopped by vacuum tube stop 26. Alternatively, vacuum could be ducted through ring support 32 and drive assembly 110 to obviate vacuum connection tube 22, with the vacuum hose in that case connected only to drive assembly 110 at any convenient location, such as adjacent to or even within control hose 410 (FIG. 5).

Referring to FIG. 10, which is a bottom view, and cross-section FIG. 11, positioning ring support 32 preferably includes retention feature 34 having detent 35. Retention feature 34 slides into matching recess 120 in drive assembly 110. Captured ball 117 settles into detent 35 under the pressure of captured spring 115 to properly locate positioning ring assembly 20. Then, thumbscrew 118 secures retention feature 34, seating it firmly against the sides of recess 120 formed in head 112 of drive assembly 110. Alternatively, thumbscrew 114 (e.g. FIG. 5) may be used from the opposite side of drive unit head 112 to secure positioning ring assembly 20.

As discussed with regard to blade fork assembly 60, a variety of materials may be used for positioning ring 20. The choice depends on whether sterility is to be ensured by reuse of the element in conjunction with a sterilization method, or by using sterile disposable elements. Suitable materials include metals, such as stainless steel, and plastics, such as polycarbonate, polysulfone, polypropylene or others.

Drive Assembly

Figure 12:
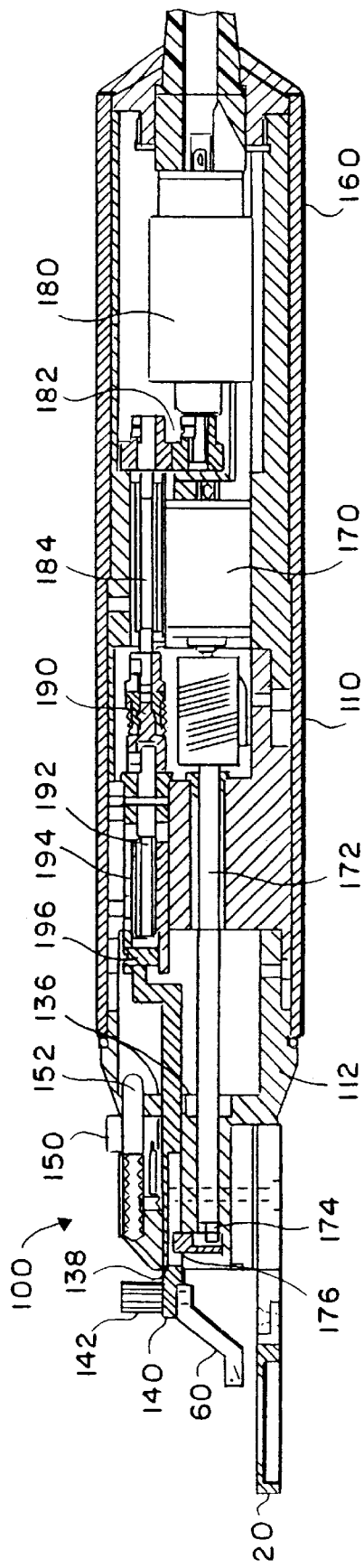
FIG. 12 shows a cross-section of a surgical unit using motor driven blade oscillation.
Figure 13:
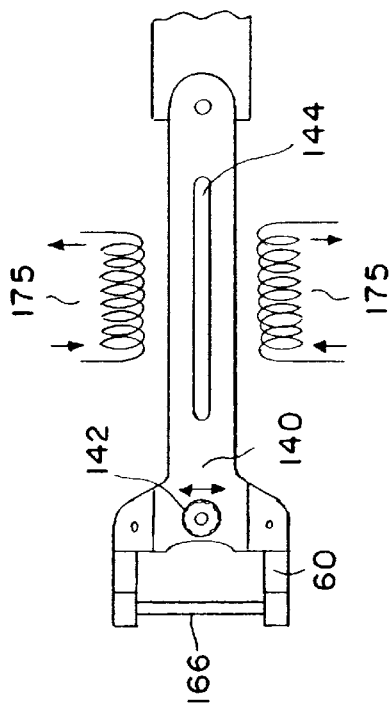
FIG. 13 shows alternative features for the surgical unit to permit field-driven blade oscillation.

FIGS. 12 & 13 show details of a preferred embodiment for surgical unit 100, and in particular shows details of a preferred embodiment for drive assembly 110, which is largely enclosed by drive assembly cover 160.

Referring to FIG. 12, the primary actuators within drive assembly 110 are travel motor 180 and oscillation motor 170. Travel motor 180 drives shaft 184 through gear train 182. Clutch 190 couples a limited torque to screw 192. The rotational motion of screw 192 is converted to linear motion by threaded traveller 194. Pivot assembly 196 couples the motion from the forward end of traveller 194 to blade fork drive arm 140, while permitting drive arm 140 to oscillate rotationally about the pivot of pivot assembly 196. Blade travel stop adjust knob 150 preferably rotates a threaded member which adjustably stops blade fork drive arm 140 travel.

Drive arm 140 preferably includes portions of its top and bottom surface which are made closely parallel to each other and a controlled distance apart (the top and bottom surfaces are those most distal from the center of drive arm 140 in the direction parallel to the pivot axis of pivot assembly 196, with the top surface being the farther from positioning ring 30). Drive arm 140 top and bottom surfaces are preferably flat to within 0.005 mm over their travel range of 1.5 cm, and are slidably captured by bearing surfaces 136 and 138 of drive assembly head 112. The bearing surfaces limit top-to-bottom play of drive arm 140 to preferably 0.01 mm or even more preferably to 0.05 mm.

Drive assembly head 112 holds positioning ring assembly 20 and blade fork drive arm 140 such that blade fork assembly 60 is maintained a known distance away from positioning ring 30 as the blade fork travels. The distance between blade 66 and applanation shoe 50 is preferably controlled to within +/−0.5 mm, or more preferably within +/−0.25 mm.

Oscillation is imparted to drive arm 140 by slider 176 which oscillates in a direction perpendicular to the page. Slider 176 interferes with the edges of a groove in drive arm 140, while the groove allows drive arm 140 to travel in and out of drive assembly 110. Slider 176 receives oscillation drive from oscillation motor 170 via shaft 172 and eccentric pin 174. Eccentric pin 174 rides in a slot in slider 176 which absorbs the vertical component of eccentric pin 174, but transmits the lateral motion.

ALTERNATIVE EMBODIMENTS OF THE INVENTION

It will be appreciated by those skilled in the art that many alternative embodiments are envisioned within the scope of the present invention. Some possible variations of the blade fork assembly are discussed in the blade fork assembly section above. Variations of other parts are discussed below, but do not represent an exhaustive survey of possibilities; rather, they serve as examples to show that a wide variety of mechanisms are encompassed within the scope of the invention.

FIG. 13 shows an alternative embodiment of means to impart oscillating motion to drive arm 140. In this embodiment drive arm 140 incorporates ferromagnetic material 144 which is acted on by magnetic fields generated by coils 175 positioned along the sides of drive arm 140.

Myriad physical configurations of the connection interface surfaces which removably attach the blade fork assembly to the blade fork drive arm can provide the predictable positioning needed to practice the invention. The mating parts of the interface are described herein as trapezoidal or "dove-tail" but may take any form having locating features, including sawtooth, rectangular, eccentric oval, keyhole, or other shapes too numerous to enumerate.

Similarly, the means for securing the connection interface is shown herein as either a thumbscrew or a cam locking lever, but could be accomplished many other ways. To mention just a few examples, the mating parts could use magnetic attraction, spring-loaded detents, or tapered engaging pieces fitted into a recess formed partly from each of the mating parts. The mating pieces could even interfere snugly under normal conditions, and have a means to temporarily change the shape of one of the pieces to release the interference and thereby permit connecting or separating the interface. Any method known in the art to disengageably secure two pieces in a closely predictable relationship could be used.

Any blade fork can be used which is able to suspend the blade, and the guide if used, in a properly controlled position with respect to the mounting surface of the connection interface. The blade and the guide may take a multitude of shapes and comprise a multitude of materials; only a few such alternatives are discussed herein.

A preferred embodiment of this invention includes sterile disposable or sterilizable disposable cutting head elements.

A non-limiting variety of material choices suitable for such an embodiment is discussed above with respect to each cutting head element. There is no need for the various cutting head elements to be all disposable or all permanent, but a mixture of disposable and sterilizable types is also suitable.

Surgical unit actuators may be driven by any known method, including pneumatic drive methods.

User commands may be recognized in any known way, including voice command reception, and sensing user activation of sensors or switches located on the surgical unit or in other convenient places. The commands thus recognized may exert control through any combination of control elements, which may include mechanical means, direct electrical control, or intelligent electrical control with intelligence provided by any means known to the art. The command recognition and control elements could be physically located amy accessible place, and as an example could be placed largely or entirely within the surgical unit.

What is claimed is:

1. A surgical device for performing corneal resectioning comprising:
   a positioning ring to position and retain an eye, the positioning ring having an opening for a cornea of the eyeball to protrude therethrough;
   a blade assembly including a blade and a guide wherein the guide is in substantially fixed relationship to the blade; and
   a drive mechanism to drive the blade assembly with respect to the positioning ring such that a cornea protruding through the opening of the positioning ring presses against the guide while the drive mechanism impels the blade assembly to move the blade through corneal tissue.

2. The surgical device of claim 1 wherein the guide is disposed at a constant distance from the blade cutting edge, the guide having a cross-sectional area defined in a plane perpendicular to a blade longitudinal axis, the cross-sectional area having a perimeter.

3. The surgical device of claim 2 wherein the perimeter of the guide is less than 6 mm.

4. The surgical device of claim 1 wherein the blade is a first blade, further comprising a second blade in substantially fixed spatial relationship to said first blade and said guide.

5. The surgical device of claim 1 wherein the guide includes a core oriented parallel to the blade longitudinal axis and a bearing sheath annular to the core and rotatable thereabout.

6. The surgical device of claim 1 wherein the blade assembly is removeably secured and is readily removable without tools.

7. A blade assembly for use in a surgical device according to claim 6.

8. The surgical device of claim 1 wherein the positioning ring is removeably secured and is readily removable and replaceable without tools.

9. A positioning ring for use in a surgical device according to claim 8.

10. The surgical device of claim 1 wherein the blade cutting edge is sapphire.

11. The surgical device of claim 1 in which the blade assembly comprises spaced apart members and the guide and the blade are each attached at lateral extremities to the spaced apart members to define the substantially fixed relationship of the guide to the blade.

12. The surgical device of claim 1 in which the substantially fixed relationship of the guide is to the blade is that the guide is spaced forward and above the blade to define a spacing between them.

13. A method for performing corneal resectioning comprising the steps of:
   positioning an eye in a positioning ring having an opening for a cornea of the eyeball to protrude therethrough;
   attaching a blade assembly having a blade and a guide to a drive mechanism connected to the positioning ring wherein the guide is in substantially fixed relationship to the blade; and
   controlling the drive mechanism to drive the blade assembly with respect to the positioning ring whereby to at least partially separate a flap from the corneal tissue protruding through the positioning ring, the flap having a thickness substantially controlled by a spacing and orientation between the blade and the guide, without concurrently restraining the protruding cornea externally by other than the blade assembly.

14. The method of claim 13 wherein the blade is a first blade and the blade assembly includes a second blade in substantially fixed spatial relationship to said first blade and said guide.

15. The method of claim 13 wherein the guide includes a core oriented parallel to the blade longitudinal axis and a bearing sheath annular to the core and rotatable thereabout.

16. The method of claim 13 wherein the blade assembly has been removed, and including the further steps of securing the blade assembly without tools.

17. A method of assisting corneal resectioning comprising the step of supplying a blade assembly for use in the corneal resectioning method of claim 13.

18. The method of claim 17 including the step of supplying a disposable blade assembly.

19. The method of claim 13 including the further step of removeably securing the positioning ring without tools.

20. A method of assisting corneal resectioning comprising the step of supplying a positioning ring for use in the corneal resectioning method of claim 13.

21. The method of claim 13 in which the blade assembly comprises spaced apart members and the guide and the blade are each attached at lateral extremities to the spaced apart members to define the substantially fixed relationship of the guide to the blade.

22. The method of claim 13 which the substantially fixed relationship of the guide is to the blade is that the guide is spaced forward and above the blade to define a spacing between them.

* * * * *